United States Patent [19]

Attwell et al.

[11] 4,213,911
[45] Jul. 22, 1980

[54] PROCESS FOR PREPARING HIGH-MELTING CHENODEOXYCHOLIC ACID

[75] Inventors: Michael C. Attwell, Islington; Thomas F. Massiah, Agincourt; Roberto A. Vergottini, Rexdale; Peter Ziegler, Toronto, all of Canada

[73] Assignee: Canada Packers Limited, Canada

[21] Appl. No.: 958,508

[22] Filed: Nov. 7, 1978

[51] Int. Cl.$^2$ .............................................. C07J 9/00
[52] U.S. Cl. ................................................. 260/397.1
[58] Field of Search ..................................... 260/397.1

[56] References Cited

U.S. PATENT DOCUMENTS

| | | | |
|---|---|---|---|
| 3,919,266 | 11/1975 | Saltzman | 260/397.1 |
| 3,931,256 | 11/1976 | Saltzman | 260/397.1 |
| 4,014,908 | 3/1977 | Saltzman | 260/397.1 |
| 4,022,806 | 5/1977 | Frost et al. | 260/397.1 |
| 4,072,695 | 2/1978 | Saltzman | 260/397.1 |
| 4,072,695 | 2/1978 | Saltzman | 260/397.1 |

OTHER PUBLICATIONS

The Lancet, 1974, p. 1518.

Primary Examiner—Eelbert L. Roberts
Attorney, Agent, or Firm—Jesse B. Grove, Jr.

[57] ABSTRACT

A process for preparing a high-melting form of CDCA having a melting point of at least about 160° C. is disclosed which comprises the steps of:

(a) suspending at least one form of CDCA having a melting point of below 160° C. in a non-aromatic liquid hydrocarbon, preferably cyclohexane, to form a suspension having a boiling point of at least 65° C.;

(b) heating the suspension to a sufficiently high temperature of between about 65° and about 140° C., preferably between about 75° and about 100° C., during a sufficiently long period of time for converting substantially all of the CDCA into the high-melting form;

(c) recovering the high-melting form of CDCA from the suspension.

Low-melting amorphous and/or crystalline forms of CDCA, as well as CDCA-solvent inclusion complexes can be treated in the above-described process. The high-melting CDCA is obtained in form of a substantially granular powder, which is suitable to be formulated into therapeutical compositions.

12 Claims, No Drawings

PROCESS FOR PREPARING HIGH-MELTING CHENODEOXYCHOLIC ACID

BACKGROUND OF THE INVENTION

The present invention relates to a process for preparing a highly purified high-melting crystalline form of chenodeoxycholic acid (=3α,7α-dihydroxy-5β-cholanic acid).

Chenodeoxycholic acid, one of the major bile acids occurring in human bile and some animal biles, possesses valuable therapeutic properties, in that it is capable of reducing and/or dissolving cholesterol gallstones in humans, and therefore is useful in the medical treatment of gall-stones and of metabolic disorders or diseases which lead to the formation of cholesterol gall-stones.

Chenodeoxycholic acid, which hereinafter will be abbreviated as CDCA, is known to exist in several polymorphic forms. The literature reports the existence of three crystalline forms having different melting points, and of at least one amorphous form of CDCA melting around 140° C., and furthermore of crystalline CDCA/-solvent complexes melting at about 120° C. (see G. Giuseppetti et al, Il Farmaco, Ed.Sc. 33, 64, 1978). According to G. Giuseppetti et al, the crystalline polymorphic forms comprise a high-melting form having a melting point of about 168° C., and two lower melting forms having a melting point of about 138° C. and of about 119° C. respectively.

The main natural sources of CDCA are animal biles. Various procedures for isolating CDCA as such from natural animal sources have been reported (see e.g., U.S. Pat. Nos. 3,931,256 and 3,919,266). Another important partially synthetic route for obtaining CDCA comprises synthesizing CDCA from cholic acid which in turn may be isolated from animal bile (see e.g., Fieser and Rajagopalan, J. Am. Chem. Soc. 72, 5530 (1950), and Hofmann, Acta Chem. Scand. 17, 173 (1963).

Since certain of the compounds which occur together with CDCA in the bile and/or are formed during the isolation and/or synthesis of CDCA (e.g., related bile acids and esters) are known to possess hepatotoxid properties, it is of utmost importance that for therapeutic purposes a form of CDCA is used which can easily and unambiguously be characterized by its physical properties, which can be provided in highly purified form, and wherein any, even minor, contamination with impurities, e.g., the above-mentioned related compounds and/or solvent residues, can be easily recognized and subsequently be removed.

Both, CDCA conventionally prepared by isolation from animal bile material or by synthesis from cholic acid, are usually obtained in a form melting around or below 140° C. Various methods for purifying the raw product have been proposed, involving recrystallization of the CDCA from various solvent systems optionally combined with a chromatographic purification step and/or intermediate formation of salts or esters of the CDCA. Most of these methods result in purified products having a melting point around or slightly above 140° C.

For example, in the process for isolating CDCA from animal bile disclosed in U.S. Pat. Nos. 3,931,256 and 3,919,266, CDCA is separated in form of its crude barium salt which is treated with ethylacetate and HCl to obtain a solution of CDCA in ethylacetate, from which CDCA is precipitated by addition of n-hexane, yielding a form of CDCA having a melting point of 140°–142° C. (see Example V). This product may be further purified by the following methods (Examples VI–VIII): countercurrent distribution of a solution in ethylacetate/n-hexane between aqueous acetic acid and isopropylether/n-hexane, column partition chromatography on "Celite" columns containing 70% acetic acid as the stationary phase and isopropylether/n-hexane as the mobile phase, absorption chromatography of a solution in ethylacetate or acetone. No significant change of the melting point of the purified product is recorded.

In the synthetic method for preparing CDCA from cholic acid disclosed by Fieser and Rajagopalan, a form of CDCA melting at 139°–142° C. is finally recovered from its solution in ethylacetate by diluting this solution with a mixture of ethyl ether and a petroleum ether.

In the process disclosed by Hofmann, a crude acid is obtained after Wolff-Kishner reduction of the corresponding ketoacid and extraction with ether-benzene or saponification of the methyl ester of CDCA and extraction with ether. When this crude acid is dissolved in a small amount of hot ethylacetate and the solution is allowed to cool, a gel is formed which after working up yields a form of CDCA having a melting point of 133°–140° C. Twice its volume of hot heptane is added to the hot ethylacetate solution, and, upon cooling, CDCA is obtained in form of crystalline needles having a melting point of 119° C.

From The Lancet 1974, 1518, and U.S. Pat. Nos. 4,014,908 and 4,072,695, it is known that the product obtained by Hofmann is an inclusion complex wherein heptane is encaptured in the crystalline structure, and that similar needle-like crystalline inclusion complexes are obtained also in other solvent systems comprising ethylacetate-cycloalkanes and ethylacetate-alkanes. From such solvent systems the cycloalkane or the alkane are incorporated into the crystalline structure. Ethylacetate alone yields an inclusion complex with ethylacetate as the included compound. According to U.S. Pat. Nos. 4,014,908 and 4,072,695, a substantially pure solvent-free form of CDCA having a melting point of between 142°–145° C. can be obtained from the CDCA-solvent inclusion complex by dissolving the crystalline complex in methanol and evaporating to dryness, or in case of CDCA-cycloalkane complex by subjecting the crystals to drying in an oil pump vacuum at a pressure of 2 mm Hg and a temperature of 90° C. (see col. 4, lines 13–37, and Example VII), or by dissolving the crystals in an aqueous alkaline solution and re-precipitating the CDCA from the alkaline solution by addition of a mineral acid.

Furthermore, The Lancet (loc. cit.) reported the formation of a high melting form of CDCA upon heating CDCA up to temperatures above 145° C. By using differential thermal analysis the following transitions were observed with the needle-like crystalline product: an endothermic process occurs at about 120° C. and is the result of release of co-crystallized solvent. This is followed by another endothermic reaction at 142°–145° C. which is in agreement with the melting point of one crystalline form. Increasing temperature leads to an exothermic reaction between 145° C. and 160° C. corresponding with recrystallization, which is finally followed by a sharp endothermic transition at 168° C., corresponding with the melting-point of the high-melting form of CDCA. Yet, in The Lancet, no additional physical characteristics of the high melting form of CDCA and no methods for obtaining this high melting form of CDCA are given and no methods for preparing the high melting form of CDCA on a larger scale are suggested.

U.S. Pat. No. 4,022,806 discloses a method by which highly purified forms of CDCA having a low melting point (i.e. an amorphous form or a CDCA/solvent inclusion complex) can be transformed into a high melting form of CDCA having a melting point of about 166° C. This method comprises preparing an aqueous suspension of the low melting form of CDCA, seeding the suspension with crystalline high melting CDCA material, treating the suspension at a temperature not greater than 85° C. to convert the CDCA completely into material of the high melting form (see column 3, lines 28–34, and 59–68). The treatment comprises heating the aqueous suspension to a temperature not greater than 85° C. with or without subjecting it to ultrasonic vibration (see column 4, lines 24–28). This process has various disadvantages. Firstly, a high-melting crystalline seeding material is required which has to be prepared separately. Furthermore, in order to effectively carry out the method of Frost et al, highly purified low melting CDCA starting material must be used and it is advisable to first prepare the crystalline calcium salt of the low melting CDCA, taking the salt up in acetic acid to form a solution of CDCA, precipitating the CDCA therefrom by dilution with water, seeding the resulting aqueous suspension of CDCA with crystalline high melting CDCA material and treating it as described above (see column 3, lines 68 to column 4, line 30).

The German Offenlegungsschrift No. 26 13 346 discloses a process for preparing a crystalline high melting CDCA material by recrystallizing raw CDCA from acetonitrile. Recrystallization from a solution in acetonitrile has also been proposed by Frost et al as a means for preparing the high melting crystalline CDCA seeding material. Even though a high melting form of CDCA can be obtained by recrystallization from acetonitrile, the use of this solvent is highly undesirable for preparing CDCA for therapeutical purposes because of the well-known toxicity of acetonitrile. The need for handling large amounts of a toxic solvent during the process naturally provides a severe disadvantage. Furthermore, in view of the well-known tendency of CDCA to retain in its crystalline structure solvents from the solution from which it is crystallized, there is the danger that at least minor amounts of the toxic acetonitrile may be retained in the high-melting crystalline material. This, of course, constitutes a potential health hazard, in particular in view of the fact that any therapeutic treatment with CDCA will usually involve administration of CDCA over a prolonged period of time.

SUMMARY OF THE INVENTION

It is an object of the present invention to provide a process for preparing a highly purified high-melting form of CDCA which avoids the drawbacks of the above-mentioned prior art processes.

It is an object of the present invention to provide such a process by which a high-melting form of CDCA having a melting point of between about 160° and 170° C., which is highly purified and is suitable for therapeutic use, is obtained from low-melting forms of CDCA.

It is a further object of the present invention to provide a process for transforming low-melting forms of CDCA into a high-melting form of CDCA in a simple procedure which can be carried out as an additional step in a conventional process directly after recovering the low-melting form of CDCA, and does not require any cumbersome intermediate purifying steps and/or introduction of additional reagents other than those used in the recovery of the low-melting forms of CDCA.

It is a further object of the present invention to provide such a process, which does not require the use of any high-melting crystalline CDCA seeding material.

It is a further object of the present invention to provide such a process wherein a purification of CDCA takes place simultaneously with its conversion into the high-melting form and which yields a product having a low volatile content.

In order to accomplish the foregoing objects according to the present invention, there is provided a process for preparing a high-melting form of CDCA having a melting point of at least about 160° C. which comprises the steps of:

(a) suspending at least one form of CDCA having a melting point of below 160° C. in a liquid, non-aromatic hydrocarbon, preferably cyclohexane, to form a suspension having a boiling point of at least 65° C.;

(b) heating the suspension to a sufficiently high temperature of between about 65° and about 140° C., preferably between about 75° and 100° C., during a sufficiently long period of time for converting substantially all of the CDCA into the high melting form; and (c) recovering the high-melting form of CDCA from the suspension.

Low melting amorphous and/or crystalline forms of CDCA, as well as CDCA-solvent inclusion complexes can be treated in the above described process. The high-melting CDCA is obtained in form of a substantially granular powder, which is suitable to be formulated into therapeutic compositions.

Further features, objects, and advantages of the present invention will become apparent from the following detailed description of the invention.

DETAILED DESCRIPTION OF THE INVENTION AND ITS PREFERRED EMBODIMENTS

The process according to the present invention provides a simple method for converting low-melting forms of CDCA (amorphous forms, low-melting crystalline forms, and/or CDCA-solvent inclusion complexes) into the more desirable high-melting form.

Surprisingly, it has been found, that when a low-melting form of CDCA is heated to a temperature of at least 65° C. in a liquid non-aromatic hydrocarbon for a sufficient period of time, a high-melting form of CDCA having a well-defined melting point in the range of about 160° C. to about 170° C. is obtained.

The resulting high-melting form of CDCA is a substantially granular powder. It is substantially comprised of granular crystals, usually melting over a 2 to 3 degree range within 160°–170° C. without the substantial pre-shrinking and pre-softening exhibited by lower-melting products (mp~140°–145° C.).

The product also has a high degree of purity. Thin-layer chromatography indicates that if components less polar than CDCA are present in the starting material, they are reduced by the hydrocarbon leach. The residual hydrocarbon level of high-melting substantially granular form of CDCA is extremely low. The relatively high volatile content of low-melting forms, melting in the range of about 140°-145° C., is substantially eliminated. Whereas the volatile content of such starting material may vary between 1 and 3%, the volatile content of the resulting high-melting substantially granular product is usually between 0 and about 0.3.

The high-melting substantially granular form of CDCA obtained according to the present invention exhibits several advantageous properties, due to which it is especially suitable for pharmaceutical production:

1. This high-melting substantially granular form of CDCA according to the present invention is a free-flowing powder with a bulk-density of from about 0.4 to about 0.6 g/ml, which is about 2 to 3 times greater than that of low-melting forms. In addition, the high-melting product, unlike low-melting ones, does not readily become highly-charged electrostatically. These properties will facilitate handling of the CDCA, especially when it is being formulated into therapeutic compositions.

2. The high-melting form does not bind solvent strongly. Hence, it can be dried rapidly to low-solvent levels under mild conditions. On the other hand, the low-melting crystals may retain up to 5% solvent.

3. Once dry, the high-melting product shows little or no tendency to re-adsorb solvent or moisture. For example, if a thoroughly dried high-melting form of CDCA according to the present invention (from a hot cyclohexane leach) and a low-melting form of CDCA (from an ethyl acetate-hexane crystallization) are leached with cold hexane, the products obtained after filtering and then drying at 70° C. in vacuo for 18 hours contain 0.0% and 3.9% volatiles respectively. This clearly illustrates the difference in solvent-binding characteristics between the two different crystal forms. When exposed to air, the low-melting form of CDCA absorbs moisture (up to about 1.5%), whereas no such absorption of moisture takes place in the substantially granular high-melting form of CDCA according to the present invention.

4. The substantially granular high-melting form of CDCA exhibits a high heat-stability; this may be due to the absence of solvent within the crystal structure. For example, when heated at 100° C. overnight there is no change in quality as determined by GLC and TLC, whereas similarly heating a low-melting CDCA leads to the formation of degradation products which are detectable by GLC, and TLC.

5. The substantially granular high-melting form of CDCA disperses readily in water, unlike the low-melting form which is difficult to disperse in water.

The non-aromatic liquid hydrocarbons which are used by the present invention are those in which CDCA is only poorly soluble. Suitable materials are non-aromatic hydrocarbons which may be saturated or unsaturated, linear or branched, and cyclic or acyclic, in particular alkanes, alkenes, cycloalkanes and cycloalkenes, having a boiling point of at least 65° C. Suitably, non-aromatic hydrocarbons, boiling between about 65° and about 140° C., preferably between about 75° and 125° C., are used, but higher boiling hydrocarbons may also be used. Examples of particularly suitable hydrocarbons are cyclohexane (b.p. ~80.7° C.), cyclohexene (b.p. ~83.0° C.), iso-octane (b.p. ~99.3° C.), methylcyclohexane (b.p. ~100.3° C.), n-heptane (b.p. ~98.4° C.) or n-octane (b.p. ~125.6° C.).

Among the above-mentioned hydrocarbons, cyclohexane is preferred because in it the conversion of low-melting forms of CDCA into the substantially granular crystalline form of CDCA occurs readily, this substance can easily be removed from the solid CDCA after the conversion, and it is commercially available in satisfactory pure form.

If desired, small amounts of organic solvents, in which CDCA is reasonably soluble and which are miscible with the non-aromatic hydrocarbon in which CDCA is relatively insoluble, may be added. For example, cyclohexane containing from 0 to 5% of acetone may be used.

In order to effect conversion of the CDCA into the substantially granular high-melting form, a temperature of at least 65° C. is required. Suitably, the temperature is between 65° C. and about 140° C., preferably between about 70° C. and 100° C. and, most preferably about 75° C. and about 100° C. At temperatures below 70° C. (e.g., in boiling n-hexane, b.p. ~69° C.), the conversion rate becomes relatively slow and uncertain. Little or no change of the melting point of the low-melting form of CDCA occurs even after several hours of heating at reflux temperatures in cyclopentane (b.p. ~49.3° C.), benzene (b.p. ~80.1° C.), or carbon tetrachloride (b.p. ~76.7° C.) or in toluene (b.p. ~110.6° C.) at 80° C. Heating temperatures above 140° C. should be avoided, as degradation of CDCA may occur above about 140° C.

Suitably, the process according to the present invention is carried out by suspending the low-melting form of CDCA in a non-aromatic liquid hydrocarbon having a boiling point within the desired temperature range, preferably in the range of between about 75° and 100° C., most preferably in cyclohexane, and heating the suspension to reflux temperature for a sufficient period of time for substantially completing the conversion into the high-melting substantially granular form. Advisably, the heating is done in the absence of alkali or mineral acid, because the former will lead to salt formation whereas the latter will catalyze degradation of CDCA.

The reaction period may vary within a wide range, depending on the reaction temperature. Using a reaction temperature of between about 75° and 100° C., reaction periods of between about 1 and about 16 hours are suitable, whereas considerably longer periods of time may be needed at lower temperatures. Usually a satisfactory degree of conversion can be obtained within a period of between about 1 and about 5 hours, preferably about 2 and about 4, if a suspension of CDCA in cyclohexane is heated to boiling temperature.

The ratio between the amount of CDCA and the amount by volume of liquid hydrocarbon may vary from about 1:4 to about 1:20. In the case of cyclohexane, a ratio of between about 1:6 and about 1:12, in particular 1:8 and about 1:10 is most preferred.

The following examples are intended to further illustrate the present invention.

EXAMPLE 1

31.2 Kilograms of ground, low-melting CDCA (crystallized from ethylacetate-hexane; m.p. 118°-125° C. turbid melt, clears at 161° C.; volatile content 1.11%) is added to cyclohexane (190 liters) in a 50-gallon glass-lined still. The mixture is stirred, heated to reflux temperature and refluxed for 2 hours. The mixture is cooled to room temperature and the solid CDCA is separated by vacuum filtration. The solid filter cake is washed with cyclohexane (27 liters) and then is dried in a vacuum oven at 80° C. for 24 hours and at 55° C. for 48 hours. The resulting dry, white solid weighs 31.0 kilograms (99% yield). The m.p. of the dry product is 162°–163° C., and its volatile content is 0.07%.

EXAMPLES 2 TO 4

Samples of low-melting CDCA are refluxed in cyclohexane as described in Example 1 for different periods of time. The results are given in Table I below.

TABLE I

| Ex. No. | PARTS BY VOL OF SOLVENT/ 1 PART OF CDCA | REFLUX PERIOD IN HOURS | % RECOVERY | MELTING POINT °C. | % VOLATILE CONTENT |
| --- | --- | --- | --- | --- | --- |
| 2 | 20 | 16 | 97 | 162–4 | 0.11 |
| 3 | 10 | 2 | 97 | 162–4 | 0.08 |
| 4 | 10 | 1 | 93 | 162–4 | 0.13 |

EXAMPLE 5

20.0 g of CDCA (melting between 140°–165° C., shrinking and softening at 120° C.) are suspended in cyclohexane (200 ml). The slurry is stirred and heated at reflux for 2 hours, then cooled to room temperature, and filtered. The filter cake is dried in vacuo at 70° C. for 16 hours. The white, granular, free-flowing powder weighs 19.6 g and melts at 162°–164° C. (shrinking at 161° C.). The packed bulk-density of the product is about 0.5 g/ml, compared to 0.22 g/ml for the starting material.

EXAMPLE 6

20.0 g of CDCA are treated with cyclohexane as described in Example 5, except that only 4 volumes of solvent (i.e. 80 ml) were used. The dried product weighs 19.6 g, melts at 162°–165° C., and has a packed bulk-density of about 0.4 g/ml.

EXAMPLE 7

5.0 g of CDCA (m.p. 120°–143° C.) are refluxed in cyclohexane (50 ml) for one hour. The slurry is cooled, and the product is isolated as described in Example 5. It weighs 4.6 g and melts at 161°–164° C.

EXAMPLE 8

2.0 g of CDCA (m.p. 140°–145° C., shrinking at 115° C.) are stirred and heated in cyclohexane (20 ml) at 74°–77° C. for 2 hours. The slurry is cooled, and the product isolated as described in Example 5 to give 1.8 g of CDCA melting at 162°–165° C. (softening at 160° C.).

EXAMPLE 9

4.0 g of CDCA (m.p. 140°–165° C., shrinking and softening at about 120° C.) are stirred at reflux in cyclohexene (40 ml) for 1 hour. The slurry is cooled to room temperature and filtered. After drying in vacuo at 80° C. for 4 hours, the filter cake, a white powder, weighs 3.4 g and melts at 162°–164° C.

EXAMPLE 10

4.0 g of CDCA (m.p. 140°–165° C., shrinking and softening at 120° C.) are stirred at reflux in n-heptane (40 ml). Samples removed after 2 and 4 hours at reflux have melting points of 161°–163° C. after filtration and drying at 80° C. in vacuo.

EXAMPLE 11

5.0 g of CDCA (m.p. 140°–145° C., shrinking at 115° C.) are refluxed in methylcyclohexane (50 ml) for 2 hours. Subsequent isolation as described in Example 5 affords 4.6 g of white crystals which melt at 162°–164° C. (shrinking at 161° C.).

EXAMPLE 12

Treatment of chenodeoxycholic acid (5.0 g) as described in Example 11 but using iso-octane (50 ml; 2,2,4-trimethylpentane) yields 4.6 g of CDCA which melts at 162°–164° C. (shrinking at 160° C.).

EXAMPLE 13

5.0 g of CDCA (m.p. 140°–145° C., shrinking at 115° C.) are stirred and heated at 90°–100° C. in n-octane (50 ml) for 2 hours. The slurry is cooled to room temperature and filtered. After drying, the product weighs 4.7 g and melts at 162°–164° C. (shrinking at 160° C.).

EXAMPLE 14

20.0 g of CDCA (m.p. 159°–161° C.) are re-crystallized from ethyl acetate (500 ml) and n-heptane (300 ml) to yield 18.6 g white crystals which melt at 117°–120° C. This procedure has been described in U.S. Pat. Nos. 4,014,908 and 4,072,695.

A portion (5.0 g) of the low-melting product, thus obtained, is refluxed in cyclohexane (50 ml) for 3 hours. The slurry is cooled to room temperature and filtered. The filter cake is dried to give 4.6 g of powder melting at 163°–165° C.

EXAMPLE 15

5.0 g of CDCA (m.p. 120°–160° C., shrinking and softening at 114° C.) are refluxed in a mixture of cyclohexane (47.5 ml) and acetone (2.5 ml) for 2 hours. The slurry is cooled and worked up as described in Example 5. The white powder weighs 4.8 g and melts at 160°–162° C. (shrinking at 159° C.).

What is claimed is:

1. A process for preparing a high-melting form of chenodeoxycholic acid having a melting point of at least about 160° C. which comprises the steps of:
    (a) suspending at least one form of chenodeoxycholic acid having a melting point of below 160° C. in a non-aromatic, liquid hydrocarbon having a boiling point of between about 65° and 140° C. to form a suspension having a boiling point of at least 65° C.;
    (b) heating the suspension to a sufficiently high temperature of between about 65° and about 140° C. during a sufficiently long period of time for converting substantially all of the chenodeoxycholic acid into the high-melting form; and
    (c) removing the high-melting form of chenodeoxycholic acid from the suspension.

2. The process as defined in claim 1, wherein the non-aromatic, liquid hydrocarbon is selected from the group consisting of alkanes, alkenes, cycloalkanes, cycloalkenes, and mixtures thereof.

3. The process as defined in claim 1, wherein the non-aromatic, liquid hydrocarbon has a boiling point of between 70° C. and about 140° C.

4. The process as defined in claim 3, wherein the non-aromatic, liquid hydrocarbon has a boiling point of between about 75° C. and about 125° C.

5. The process as defined in claim 4, wherein the non-aromatic, liquid hydrocarbon is selected from the group consisting of cyclohexane, cyclohexane, methylcyclohexane, n-heptane, n-octane, iso-octane, and mixtures thereof.

6. The process as defined in claim 5, wherein the non-aromatic, liquid hydrocarbon is cyclohexane.

7. The process as defined in claim 6, wherein the suspension further comprises between 0 to about 5% of acetone.

8. The process as defined in claim 1, wherein the temperature is between about 75° C. and about 100° C.

9. The process as defined in claim 8, wherein the period of time is between about 1 and about 16 hours.

10. The process as defined in claim 9, wherein the period of time is between about 1 and about 5 hours.

11. The process as defined in claim 1, wherein the non-aromatic, liquid hydrocarbon is present in an amount of between about 4 and about 20 parts by volume per 1 part of chenodeoxycholic acid.

12. The process as defined in claim 6, wherein the cyclohexane is present in an amount of between about 6 and about 12 parts by volume per 1 part of chenodeoxycholic acid.

* * * * *